United States Patent [19]
Poland

[11] Patent Number: 6,080,107
[45] Date of Patent: Jun. 27, 2000

[54] METHODS FOR THE USE OF CONTRAST AGENTS IN ULTRASONIC IMAGING

[75] Inventor: Mckee D Poland, Andover, Mass.

[73] Assignee: Hewlett-Packard Company, Palo Alto, Calif.

[21] Appl. No.: 09/237,391

[22] Filed: Jan. 26, 1999

[51] Int. Cl.[7] .......................................................... A61B 8/00
[52] U.S. Cl. ............................................................. 600/458
[58] Field of Search .................................... 600/443, 447, 600/458

[56] References Cited

U.S. PATENT DOCUMENTS

| | | | |
|---|---|---|---|
| 5,255,683 | 10/1993 | Monoghan | 128/662 |
| 5,560,364 | 10/1996 | Porter | 600/458 |
| 5,577,505 | 11/1996 | Brock-Fisher et al. | 128/662 |
| 5,694,937 | 12/1997 | Kamiyama | 600/447 |
| 5,735,281 | 4/1998 | Rafter et al. | 600/458 |
| 5,833,613 | 11/1998 | Averkiou et al. | 600/440 |
| 5,833,615 | 11/1998 | Wu et al. | 600/458 |
| 5,860,931 | 1/1999 | Chandler | 600/458 |
| 5,944,666 | 8/1999 | Hossack et al. | 600/458 |
| 5,947,904 | 9/1999 | Hossack et al. | 600/458 |
| 5,957,845 | 9/1999 | Holley et al. | 600/443 |

OTHER PUBLICATIONS

"Transient Myocardial Contrast After Initial Exposure To Diagnostic Ultrasound Pressures With Minute Doses Of Intravensouly Injected Microbubbles", Dr. Thomas Porter, et al. Circulation, vol. 92, (1995), pp. 2391–2395.

*Primary Examiner*—Francis J. Jaworski

[57] ABSTRACT

Methods for use of contrast agents with an acoustic echographic imaging system, including controlling the concentration of contrast agent in a region of interest by adjusting the acoustic imaging signal to increase or decrease depletion of the contrast agent to the linear range of response. Adjustment of the signal includes dividing the received signal level by a power reduction ratio to re-normalize the signal level and compensating the signal power level. A spectral processor detects the concentration of the contrast agent in a gate marker window as the averaged ratio of energy around the second harmonic of the return signal versus energy around the fundamental frequency of the return signal, and includes a boundary detector for detecting a point of greatest change in value of the averaged ratios as a boundary between regions of interest. A well defined bolus of contrast agent in a region of interest is created by scanning to destroy contrast agent entering the region of interest during a predetermined initial interval. A desired contrast agent depletion patterns is generated by scanning a selected portion of the region of interest with a depletion acoustic signal having a power level and duration selected to create a desired contrast agent depletion pattern. The depletion acoustic signals may be separate and different from the acoustic image signals in one or more signal characteristics, including the arrangement, sequence, frequency, pulse length, number of pulses, power levels, focus profiles, apodization and apertures.

21 Claims, 5 Drawing Sheets

METHODS FOR THE USE OF CONTRAST AGENTS IN ULTRASONIC IMAGING

TECHNICAL FIELD

The present invention relates to improved methods and apparatus for use of a contrast agent in ultrasonic imaging and, in particular, to improved methods and apparatus for the detection and measurement of contrast agents in regions of interest and the creation of well defined boluses of contrast agent in regions of interest.

BACKGROUND ART

Ultrasonic transducers and imaging systems are used in many medical applications and, in particular, for the non-invasive acquisition of images of organs and conditions within a patient, typical examples being the ultrasound imaging of fetuses and the heart. Such systems commonly use a linear or phased array transducer having multiple transmitting and receiving elements to transmit and receive narrowly focused and "steerable" beams, or "lines", of ultrasonic energy into and from the body. The received beams, or lines, are reflected from the body's internal structures and contain amplitude or phase information, or both, that is used to generate images of the body's internal structures.

A primary problem in ultrasonic imaging has been that many of the body's internal structures have similar characteristics as regards the reflection of ultrasonic energy, so that it is difficult to obtain as clear and detailed images of many of the structures as is desired. In particular, many of the structures of interest, such as the muscles of the heart, are perfused with blood, so that it is difficult to distinguish between blood vessels and the chambers of the heart and the heart muscles.

This problem led to the development of alternative methods for imaging certain of the body's structures, such as the blood vessels of the heart. One of the most common imaging techniques, for example, is referred to as an angiogram and requires the injection of a radiofluorescent dye into the vessels to image the blood vessels of the heart with x-rays. Such techniques, however, are invasive or are otherwise unsatisfactory. For example, the use of x-ray imaging carries the risk of potential injury from radiation and involves complex, expensive and hazardous equipment. Also, radiofluorescent dyes are potentially toxic to at least some patients and are not broken down in the body but are flushed from the body by natural waste processes, often requiring hours to disappear from the body.

A more recent development has been ultrasonic imaging using contrast agents injected into the blood stream. Ultrasonic contrast agents are now commercially available and are essentially small bubbles of gas, such as air, formed by agitating a liquid or bubbling gas through a liquid, such as a saline solution or a solution containing a bubble forming compound, such as albumin. When insonicated, the bubbles resonate at their resonant frequency and emit energy at both the fundamental and second harmonic of their resonant frequency, thereby returning an enhanced signal at or around these frequencies and thereby providing an enhanced image of the liquid or tissue containing the contrast agent. It is also well known that the bubbles "disappear" when insonicated and the current theory is that the insonication ruptures the bubble's shell, thereby allowing the gas to dissipate into the surrounding liquid or tissue.

The use of ultrasonic contrast agents is thereby advantageous in allowing enhanced imaging using ultrasonics rather than x-rays, thereby eliminating the radiation hazard and allowing the use of equipment that is significantly less expensive and hazardous to use. Also, the agents are non-toxic and dissolve relatively quickly into waste products, such as air and albumin, that are normally found in the body and that are themselves non-toxic. Further, the insonication of the agent in itself destroys the agent, so that the agent can effectively be "erased" during the imaging process to a degree.

There are, however, a number of persistent problems in ultrasonic imaging using contrast agents. For example, it is important to be able to measure the rate of blood flow through tissues such as the heart muscles in order to detect damaged tissues or tissues having insufficient blood flow, such as may occur when an artery is partially or completely blocked. While there have been attempts to measure the perfusion of blood containing a contrast agent in tissues such as the heart muscles to thereby measure the volume of blood in the heart tissues, the results have been unsatisfactory because blood volume is not directly dependent on rate of blood flow.

Yet another problem is control of the concentration of contrast agent in a region of interest. That is, it is well known that the concentration of contrast agent in a region of interest is critical to the images obtained therefrom because the intensity of the image, that is, the amplitude of the returned scanning signal, will increase with an increase in concentration of the contrast agent up to a certain point, and will then plateau. As a consequence, too low a concentration will result in poorly enhanced images. Too high a concentration, however, will result in agent saturation and "washing out" of at least portions of the image as the concentration of agent in the corresponding volumes of tissue reach the plateau concentration, so that various volumes of the tissue cannot be distinguished by differences in concentrations of the agent.

While there are various reasons for this effect, one is that the saturation of agent particles in a given region results in a non-linear increase in intensity in the image due to interference between the particles that reduces the total reflection. This effect appears to become significant when the concentration is such that the particles or bubbles are, on the average, within one transmit frequency wavelength of each other.

Another related problem is a shadowing effect wherein the ultrasonic energy is absorbed or reflected by the agent in a bolus or body of the agent in the near field of the scan line, that is, when a volume of agent that is nearer to the transducer than the region of interest generates a return that overshadows the return from the region of interest. Since the ultrasonic energy that reaches the region of interest is thereby attenuated more than what would normally be returned from the effects of the tissue in the region of interest, the return signal is of a lower intensity than normal and the density of contrast agent in the region of interest is therefore underestimated. Accordingly, and for example, a spatial average measure of intensity in a region of interest that included a shadowed region would underestimate the concentration of contrast agent therein, resulting in degradation of the resulting image. Too high a concentration of contrast agent in the regions between the transducer and the region of interest will thereby result in a shadowing effect wherein the near region image return will shadow, that is, hide or at least degrade the image in the region of interest.

Yet another related problem arising from an inability to control the concentration of contrast agent in a region of interest is a result of the depletion of the contrast agent as a side effect of the normal imaging process if the concentration of agent is too high. That is, if the contrast agent is too concentrated, it tends to absorb the acoustic energy of the scan beam in the near field of the acoustic transducer, thereby not only shadowing the agent in the far-field of the transducer beam as described above but also resulting in disproportionate depletion of the agent in the near field relative to the depletion of the agent in the far-field. This differential depletion, in turn, interferes with the detection and measurement of the agent in the far field.

Still other problems are related to the detection and measurement of the actual concentration of contrast agent in tissues of liquids, rather than the mere presence of a contrast agent, because it is difficult to detect boundaries between liquids and tissues, particularly as the agents permeate both the liquid transporting the agent, such as blood, and the tissues because the agents are transported into the tissues with the blood.

Another and related problem associated with the use of ultrasonic contrast agents arises from the practice that, like radiofluorescent dyes, the agents are preferably introduced into the body through a vein, where the blood is at a relatively low pressure, rather than an artery, where the blood is at a relatively high pressure. As a consequence, the agent must flow through a considerable path through the body, such as the lungs and the heart, before reaching the regions of interest, such as the arteries and chambers of the heart. The contrast agent therefore does not reach the region of interest as a sharply defined "bolus" or body of agent enhanced blood, but as a diffuse "cloud" that increases and decreases in concentration gradually.

The object of the process, however, is to differentiate between healthy tissue, which perfuses rapidly, and stunned, hibernating or infarcted tissue, which perfuses slowly, if at all. When the bolus appears at the tissues of interest as a diffuse cloud, the enhancing agent will often perfuse into the tissue at a rate that is determined by the gradient of the edge of the cloud rather than by the perfusion rate of the tissues, and a rate that is often less than the perfusion rate of healthy tissue. As a result, the delineation between healthy and infarcted tissues is blurred and the resulting image is of low resolution.

The prior art has attempted to solve this problem for radiofluorescent dyes by using a catheter introduced into an artery as far as possible from the heart, such as at the upper leg, and passed through the arteries to the region of the heart to transport the dye to a point near or in the heart before introducing the dye into the bloodstream. This procedure, however, is invasive and risks damage to the arteries or heart and it is often difficult to prevent or stop subsequent bleeding from the artery at the point the catheter was inserted.

The present invention provides a solution to these and other problems of the prior art by providing improved methods for the use of contrast agents.

DISCLOSURE OF THE INVENTION

In a first aspect, the present invention is directed to a method for use with an acoustic echographic imaging system for controlling the concentration of contrast agent in a region of interest to within a range of generally linear response wherein the contrast agent is depleted by an amount related to the power level of the acoustic imaging signal insonicating the contrast agent.

The acoustic imaging system includes a transducer for transmitting an acoustic imaging signal and receiving a return signal representing an image along a scan line, the return signal including contributions from a contrast agent, and a processor for generating the acoustic imaging signal and extracting from the return signal information representing the concentration of contrast agent along the scan line. The method for controlling the concentration of contrast agent includes the steps of determining from the return signal the relative concentration of contrast agent along the scan line and, from the relative concentration of the contrast agent, adjusting the characteristics of the acoustic imaging signal to increase depletion of the contrast agent when the concentration of contrast agent is higher than the linear range of response and decreasing the depletion of the contrast agent when the concentration of contrast agent is lower than the tissue intensity or linear range of response.

Adjusting the characteristics of the acoustic imaging signal includes dividing the received signal level by a power reduction ratio, such as the time interval elapsed since the last scan, thereby re-normalizing the received signal level at each scan and compensating for the effects caused by variation of the transmitted power or increasing the power level of a next acoustic imaging signal by an amount to deplete the contrast agent from a saturation level of concentration.

A further aspect of the present invention is directed to a spectral content measurement processor and a corresponding method for detecting the concentration of the contrast agent along the scan line.

The spectral content measurement processor includes a gate marker generator for generating a gate marker window for selecting at least one scan line and a position in the gate marker window along the selected scan line and a signal buffer connected to receive a return signal along the scan line and responsive to the gate marker signal to capture the return signal in the gate marker window. A second harmonic component energy detector then provides a second harmonic energy signal representing the second harmonic energy within the frequency band around the second harmonic of the captured return signal versus axial position along the selected scan line as the gate marker window is moved along the selected scan line. A fundamental frequency component energy detector provides a fundamental frequency energy signal representing the fundamental frequency energy within the frequency band around the fundamental frequency of the captured return signal versus axial position in the gate marker window and along the selected scan line as the gate marker window is moved along the selected scan line.

A ratio determiner then receives the fundamental frequency energy signal output and the second harmonic energy signal output and generates a ratio output representing the proportion of second harmonic energy to fundamental frequency energy versus position of the gate marker window along the selected scan line. A ratio averager, in turn, receives the ratio output and is responsive to the gate marker window for selecting, in a sub-window of the gate marker window, the ratio output along the scan line and generates an averaged ratio output for each selected window of the ratio output wherein an averaged ratio output represents the concentration of contrast agent in the selected window.

In a present embodiment, the spectral content measurement processor repeats the generation of the averaged ratio output at each iteration of the acoustic imaging signal so that the averaged ratio output for each selected window represents the averaged harmonic ratio versus time along the scan line, thereby representing the contrast agent concentration along the selected scan line as a function of time.

In a presently preferred embodiment, the second harmonic component energy detector includes a second harmonic mixer for mixing the captured return signal and a second harmonic mixer signal to generate a resultant second harmonic mixed signal, a low pass filter for filtering the resultant second harmonic mixed signal to generate a band limited low filtered second harmonic signal, and a final second harmonic filter for squaring and spatially averaging the low filtered second harmonic signal and providing the second harmonic energy signal output. The fundamental frequency component energy detector in turn includes a fundamental frequency mixer for mixing the captured return signal and a fundamental frequency mixer signal to generate a resultant fundamental frequency mixed signal, a low pass filter for filtering the resultant fundamental frequency mixed signal to generate a band limited low filtered fundamental frequency signal, and a final fundamental frequency filter for squaring and spatially averaging the low filtered fundamental frequency signal and providing the fundamental frequency energy signal output.

In a yet further embodiment of the present invention, the spectral content measurement processor further includes a boundary detector for detecting a boundary between regions of interest. The boundary detector includes the gate marker generator for selecting a scan line passing through the boundary between the regions of interest and for incrementally stepping the gate marker sub-window along the scan line, and a comparator for comparing the values of the averaged ratio at each step of the sub-window along the scan line and identifying the point of greatest change in value of the averaged ratios along the scan line, thereby identifying the point of greatest change in value of the averaged ratios along the scan line as the point of the boundary between the regions of interest.

The present invention further includes a method for creating a well defined bolus of contrast agent in a region of interest being scanned with the acoustic imaging signal. According to the present invention, the method includes introducing a flow of contrast agent into the region of interest, scanning the region of interest with an acoustic signal having a power level selected to destroy the contrast agent entering the region of interest at a rate to keep the concentration of contrast agent in the region of interest to a predetermined low, steady state level. After a predetermined time has passed since the flow of contrast agent has begun, the end of that time being designated by a user of the system as the beginning of perfusion of the region of interest by a flow of contrast agent of a desired concentration, the power level of the acoustic signal is reduced, and the system begins image scanning of the region of interest at an acoustic imaging signal power level less than that selected to destroy the contrast agent.

In a further embodiment, the method of creating a well defined bolus of contrast agent in a region of interest further includes the step of detecting the concentration of the contrast agent in the region of interest by measuring from a returned acoustic signal the spectral content of the return signal.

The present invention also provides a method for generating desired contrast agent depletion patterns or for compensating for unwanted contrast agent depletion patterns in a region of interest and resulting from destruction of the contrast agent by the acoustic signal. The method includes the steps of scanning the region of interest with an acoustic imaging signal selected to provide a return signal representing an image of the region of interest along at least one scan line, and scanning at least a selected portion of the region of interest with a depletion acoustic signal having a power level and duration selected to create a desired contrast agent depletion pattern.

In another aspect, the method for generating desired contrast agent depletion patterns or compensating for unwanted contrast agent depletion patterns may include the step of generating and transmitting the depletion acoustic signal in the interval between scans of the region of interest with the acoustic image signal, the depletion acoustic signal not being used for the generation of an image display and the power level and duration of the depletion acoustic signal being selected to be completed in the interval between scans with the acoustic image signal. Alternatively, the method may include scanning the region of interest with an acoustic imaging signal selected to provide a return signal representing an image of the region of interest along at least one scan line, and scanning at least a selected portion of the region of interest with a depletion acoustic signal selectively focused into the imaging scan far field and having a power level and duration selected to create a desired contrast agent depletion level, for example, to deplete the level of contrast agent in the imaging scan far field to levels corresponding to the level of contrast agent in the imaging scan near field. In either embodiment, the depletion acoustic signal may be generated and transmitted in the interval between image scans of the region of interest with the acoustic image signal, with the power level and duration of the depletion acoustic signal being selected to be completed in the interval between scans with the acoustic image signal. In yet other embodiments, the depletion acoustic signals will be separate and different from the acoustic image signals and will differ from the acoustic image signals in one or more signal characteristics wherein the signal characteristics include the arrangement, sequence, frequency, pulse length, number of pulses, power levels, focus profiles, apodization and apertures. In certain embodiments, the depletion acoustic signals may be executed in a separate frame from the acoustic image signals.

Other features, objects and advantages of the present invention will be understood by those of ordinary skill in the art after reading the following descriptions of a present implementation of the present invention, and after examining the drawings, wherein:

BEST MODE FOR CARRYING OUT THE INVENTION

The following will first describe a generalized ultrasonic echographic system in which the present invention may be implemented, and will then describe individual aspects of the present invention in detail.

A. General Description of an Ultrasonic Echographic System (FIG. 1)

Figure 1:
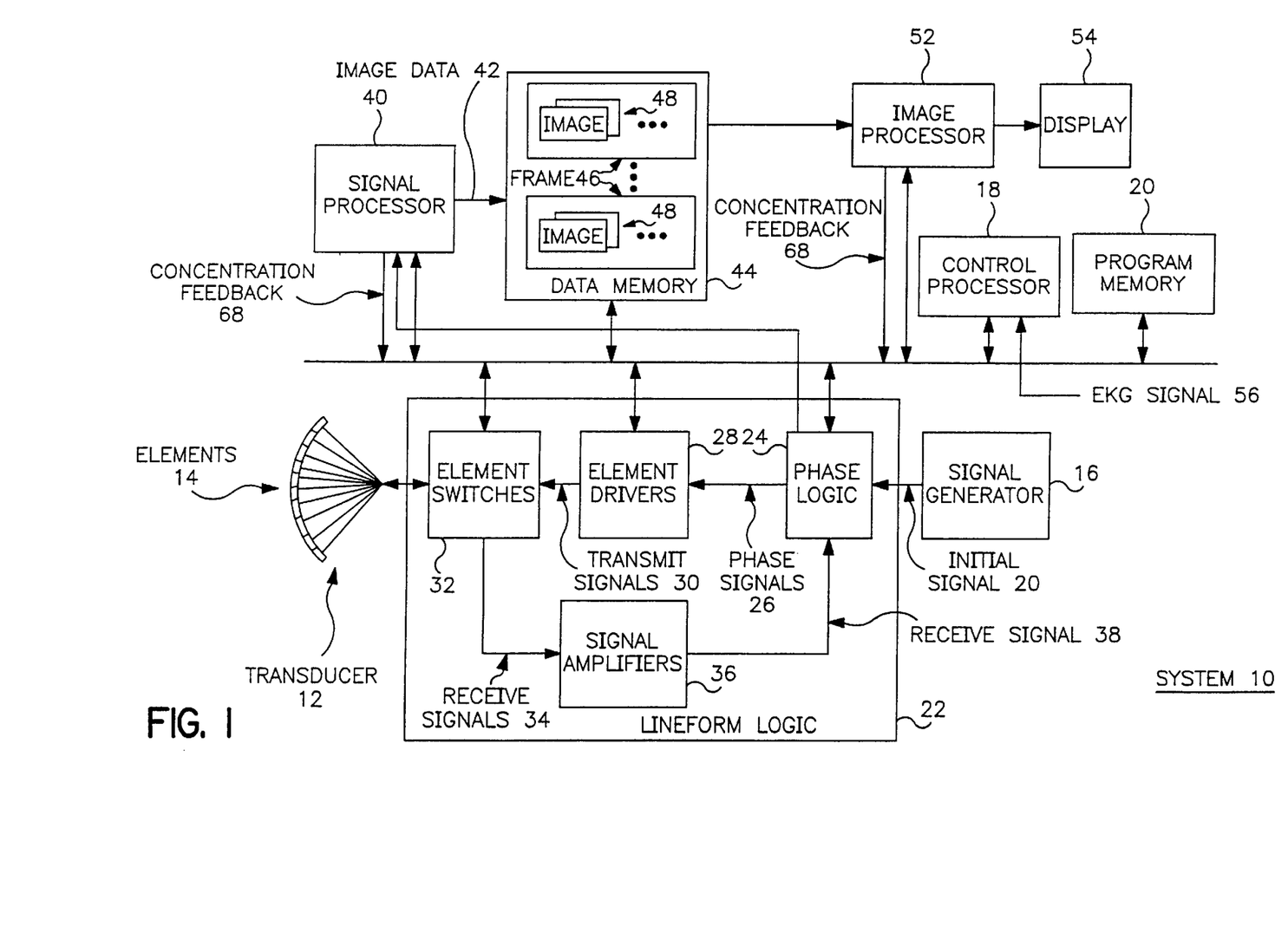
FIG. 1 a diagrammatic block diagram of an ultrasonic echographic system.

Referring to FIG. 1, therein is presented a diagrammatic block diagram of an ultrasonic echographic System 10 in which the present invention may be implemented. It will be appreciated by those of ordinary skill in the relevant arts that System 10 as illustrated in FIG. 1, and the operation thereof as described herein below, is intended to be generally representative of such systems and that any particular system may differ significantly from that shown in FIG. 1, particularly in the details of the construction and operation of such as system. As such, the System 10 represented in FIG. 1 is to be regarded as illustrative and exemplary and not as limiting as regards the invention described herein or its implementations and embodiments or the claims hereto.

As illustrated in FIG. 1, and as is well known and understood in the relevant arts, a typical System 10, such as a Hewlett-Packard Sonos 2500, includes a Transducer 12 for transmitting lines, that is, beams, of ultrasonic energy into a body and receiving the ultrasonic energy reflected from the internal structures of the body, including energy at the first harmonic and second harmonic frequencies of a contrast agent present in the path of the current line. A Transducer 12 is generally comprised of an array of piezoelectric Elements 14 that may be used individually or in combinations to form and steer the transmitting and receiving lines of Transducer 12. As is also well understood in the relevant art, the formation of transmitting lines by a Transducer 12 is accomplished by the selection of individual Elements 14 to comprise an aperture for each transmitting or receiving line and the driving of the selected Elements 14 by signals having selected phase relationships. Receiving lines are formed in the same manner, except that the received "signal" is comprised of a received signal from each of the selected Elements 14 and the phase relationships of the individual received signals are controlled to form a single received signal forming the received line.

For this purpose, System 10 includes a Signal Generator 16 that may be controlled by a programmed Control Processor 18 operating under control of programs stored in a Program Memory 20 to generate an Initial Signal 20 at a selectable frequency. Initial Signal 20 is provided to Lineform Logic 22 that includes Phase Logic 24 that operates under program control of Control Processor 18 to generate a plurality of Phase Signals 26. There is at least one Phase Signal 26 for each Element 14 of a currently selected aperture of Transducer 12 and Phase Logic 24 controls the phase relationships between the Phase Signals 26 of the current aperture to provide the phase relationships necessary for the line generated by the current aperture. Phase Signals 26 are then provided to Element Drivers 28, which operate under programmed control of Control Processor 16 to amplify Phase Signals 26 to a selectable power level or levels required for the currently generated transmitting line.

The amplified outputs of Element Drivers 28, indicated in FIG. 1 as Transmit Signals 30, are then provided to Element Switches 32 which are essentially demultiplexer/multiplexer switches to route Transmit Signals 30 to the selected ones of Elements 14 forming the current transmit aperture of Transducer 12. The selected Elements 14 then transmit corresponding ultrasonic signals into the body being imaged.

Element Switches 32 also operate under programmed control of Control Processor 18 to form the receiving lines of a current receiving aperture by routing the incoming Receive Signals 34 from selected Elements 14 through Signal Amplifiers 36 to Phase Logic 24. As is well known the art, the Elements 14 selected to comprise a current receiving aperture are generally the same Elements 14 as form the transmitting aperture, but need not be the same in either number of arrangement.

Phase Logic 24 then operates under programmed control of Control Processor 18 to phase shift and combine the Receive Signals 34 into a Receive Signal 38 that is provided to Signal Processor 40. As is well understood in the relevant arts, Signal Processor 40 may perform a variety of operations upon Receive Signal 38, such as low pass, high pass, and bandpass frequency filtering, separation of the signal into in phase and quadrature components, determination of doppler frequency shifts and analog to digital conversion, to generate a digital Image Data 42 output representing a received image along the current transmit/receive line.

Image Data 42 is then stored in a Data Memory 44 as a sequence or array of Frames 46 of Images 48 wherein each Image 48 is comprised of the data representing a received signal along a corresponding line of Transducer 12. A single Frame 46 may contain, for example, successive Images 48 taken along a single line during a complete cardiac cycle, so that the array of Frames 46 together comprise a complete set of Images 48 taken along each line of Transducer 12 and over one or more cardiac cycles. It will be noted that, particularly in the instance of cardiac imaging, the operation of System 10 in generating transmit lines, switching between lines and organizing Frames 46 and Images 48 will frequently be synchronized to the cardiac cycle through use of an EKG 50 signal provided as an input to Control Processor 18.

Image Data 42 may then be processed further by Image Processor 52, for example, to enhance Images 48 or to form three dimensional arrays of the data from Images 48 to generate still further images, such as different cross sectional views of the cardiac structure, and is displayed through a Display 54.

It will be understood that System 10 may generate other displays and perform yet other functions to display ultrasonic images. For example, System 10 may be used to determine and display doppler information images representing, for example, the rates and patterns of blood flow in the heart chambers and that, in this instance, Images 48 will contain doppler data and that System 10 may generate such user aids as a doppler cursor to indicate the current line and direction that doppler information is being obtained and displayed for. Also, portions of an Image 48 or a set of Images 48 may be selected and enlarged for display, thereby providing a more detailed display of selected regions of interest represented by the data in Images 48.

It will also be understood that certain of the functions that are described above as controlled by programs executed by Control Processor 18 may also be controlled manually by user input, such as the frequency and power level of the transmit lines.

B. Detailed Descriptions Of Improved Methods For Use of Contrast Agents

Having described an exemplary System 10 in which the present invention may be implemented and employed, the following will provide detailed descriptions of improved methods for using such a system with contrast agents to overcome the problems of the prior art. It will be noted that each description of an improved method for use of contrast agents will begin with a brief summary of the problem approached by the improved method, to thereby clarify the reason for and operation of the improved method.

1. General Discussion of Ultrasound Imaging of Tissue Perfusion With Contrast Agents (FIGS. 2, 3A to 3B, 4A to 4D and 5A to 5C)

Diseased or damaged tissue in the human body is often characterized by decreased perfusion, that is, rate of flow, of blood therethrough. For example, most heart attacks are caused by clotting, or blocking, of the coronary arteries feeding blood to the heart muscle tissues so that portions of the heart muscles receive a reduced blood supply until the tissue become infarcted and dies. The ability to detect tissues with reduced perfusion is therefore advantageous in detecting and diagnosing various pathologies in the organs and tissues of the body.

As described previously, contrast agents have come into use to enhance the ultrasonic imaging of tissues of the body and it is well known that not only do such agents provide an enhanced image when insonicated at their primary resonant frequency, but that many agents have non-linear frequency responses and tend to produce very strong second harmonic reflections. As a result, the ability of a System 10 to distinguish between tissues and blood containing a contrast agent and to generate corresponding images is enhanced when the received signal is filtered to emphasize the second harmonic return.

It is also known that insonication of many contrast agents at sufficient power levels, which have been established by experiment and are well known in the relevant publications, "pops" the "micro-bubbles" of a contrast agent, thereby "erasing" the agent. As a consequence, it is known that two successive scans of a region of interest containing a contrast agent, the first at a power level sufficient to obtain an image and to "destroy" the contrast agent therein and the second to thereafter obtain an image without the contrast agent thereby provides a measure of the amount of contrast agent in the region.

The systems and methods of the prior art have assumed that perfusion is proportional to the amount of blood present in the tissue in the region of interest and can thereby be determined by measuring the amount of contrast agent in the tissue. There are indications, however, that this assumption maybe incorrect, to a first order, as even poorly perfused, diseased tissue will contain approximately the same density of blood, that is, amount of blood per unit of tissue, as healthy tissue. What differentiates healthy tissue from poorly perfused tissue is therefore not the density of blood in the tissues of interest, as represented by the density of contrast agent, but the rate at which blood is exchanged through the tissue.

According to the methods of the prior art, healthy tissues may be distinguished from poorly perfused tissues by measuring the rate of exchange, that is, the rate of flow, of blood through the tissue of interest. This is accomplished by obtaining successive images of the region of interest as a contrast agent is introduced into the blood flow to the tissues of interest and subtracting the images obtained at time intervals that are selected to be proportional to the rate of perfusion of blood, with the contrast agent, into the tissues of interest and during the "wash-in" and/or "wash-out" periods of the agent. This time period has been determined to be on the order of one second, that is, approximately the time between successive Frames 46 wherein each Frame 46 is a cardiac cycle and the Frames 46 are preferably synchronized with the cardiac cycle so that subtraction is between corresponding Images 48 that were obtained at the same point in successive cardiac cycles.

Figure 2:
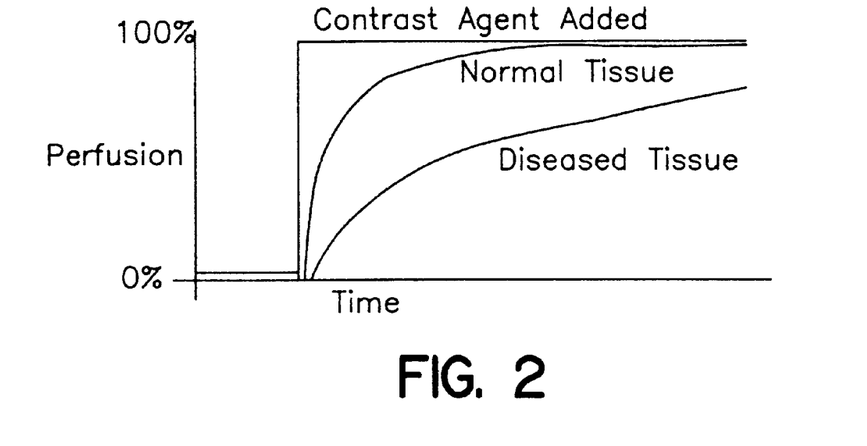
FIG. 2 illustrates the difference over time between the perfusion of diseased tissue and healthy tissue with blood containing a contrast agent.
Figures 3A, 3B, 3C, 3D:
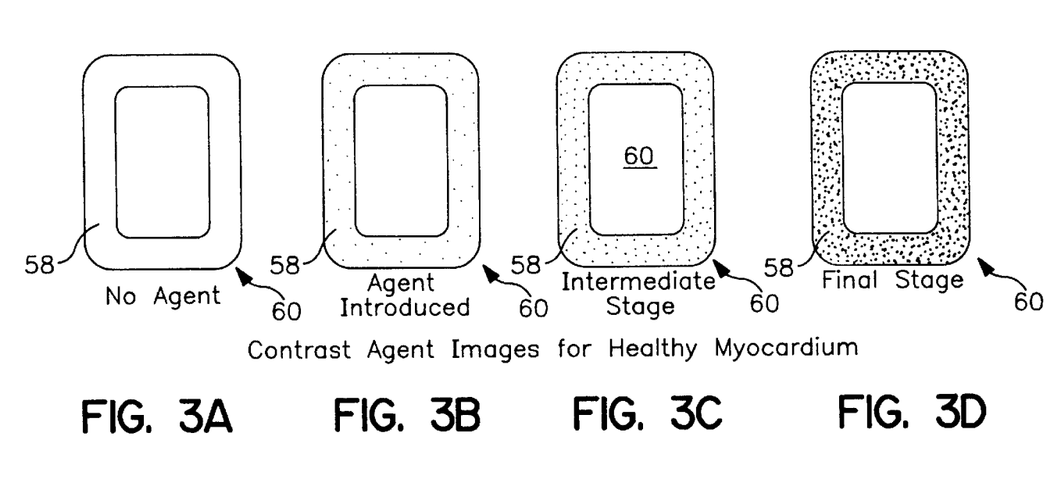
FIGS. 3A through 3D are diagrammatic representations of time sequential images of the tissues of a healthy myocardium upon the injection of a contrast agent into the blood flow to the myocardium.
Figures 4A, 4B, 4C:
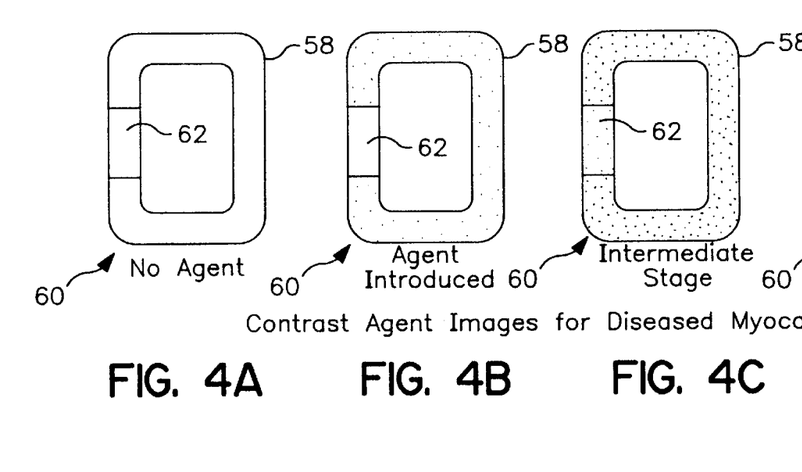
FIGS. 4A through 4D are diagrammatic representations of time sequential images of the tissues of a diseased myocardium upon the injection of a contrast agent into the blood flow to the myocardium.
Figure 4D:
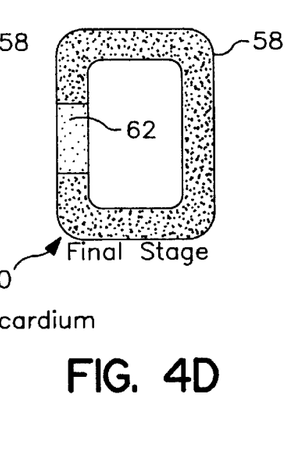

The method is illustrated in FIGS. 2, 3A through 3D, 4A through 4D, and 5A through 5C wherein FIG. 2 illustrates the difference over time between the perfusion of diseased tissue and healthy tissue with blood containing a contrast agent. FIGS. 3A through 3D, in turn, are diagrammatic representations of time sequential images, progressing from FIG. 3A to FIG. 3B, of the Tissues 58 of a healthy Myocardium 60 upon the injection of a contrast agent into the blood flow to the myocardium. FIGS. 4A through 4D, in contrast, are diagrammatic representations of time sequential images, progressing from FIG. 4A to FIG. 4B, of the Tissues 62 of a diseased Myocardium 64 having an Area 66 of diseased tissue upon the injection of a contrast agent into the blood flow to the myocardium. It will be noted between FIG. 3 and FIG. 4 that the tissues of the healthy myocardium are evenly perfused at each point in time while the tissues of the diseased myocardium are differentially perfused over time until a time, represented in FIG. 4D, whereby the tissues of the myocardium become evenly perfused. It will be noted that by the time illustrated in FIG. 4D diseased Area 66 is no longer distinguished from the healthy tissues as all tissues of the mycodardium have become evenly perfused.

Figures 5A, 5B, 5C:
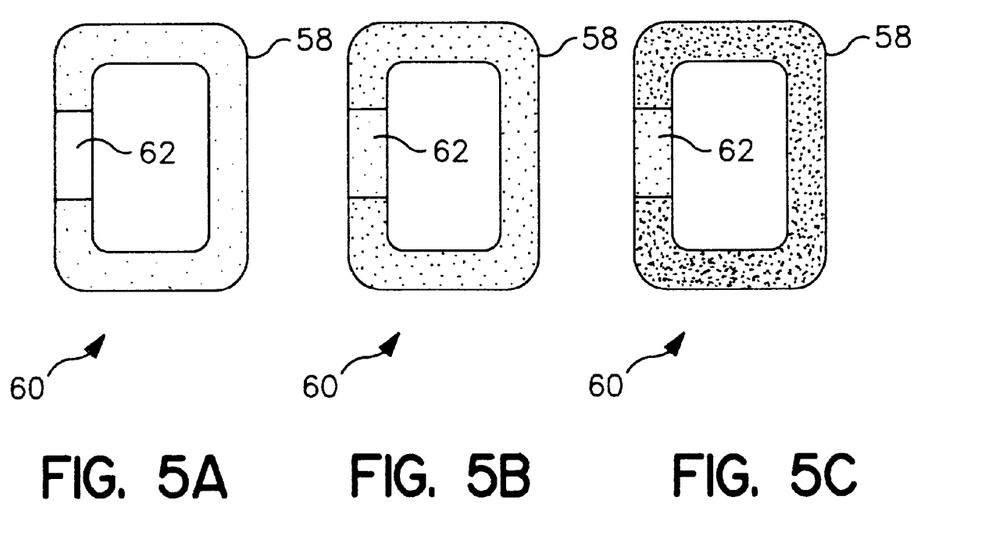
FIGS. 5A through 5C diagrammatically illustrate the images obtained by subtracting successive ultrasound images with a contrast agent.

Finally, FIGS. 5A through 5B diagrammatically illustrate the Images 48 obtained by subtracting successive images. For example, FIG. 5A is obtained by subtracting FIG. 4A from FIG. 4B, FIG. 5B by subtracting FIG. 4B from FIG. 4C, and FIG. 5C by subtracting FIG. 4C from FIG. 4D. It will be noted that diseased Area 66 is readily observable in each of FIGS. 5A through 5D.

It will be noted that the Frames 46 of the subtracted Images 48 may be obtained at separations of multiple cardiac cycles. It will also be noted that the blood flow may be displayed using colors or intensities to represent the changes in volumes of contrast agent in the tissues and thereby the rate of blood flow through the tissues, and that the resulting image may be overlaid upon or by other images derived from other signal components of the Receive Signals 34. Also, autoregressive modeling techniques may be used to model the time constants of the wash-in or wash-out periods, rather than determining the difference in volume of contrast agent, or the image difference circuitry, which effectively implements a 2 tap FIR filter, could be implemented as an IIR filter with a similar response. Also, the method may be practiced using techniques similar to thermal dilation to measure cardiac output.

Figure 7:
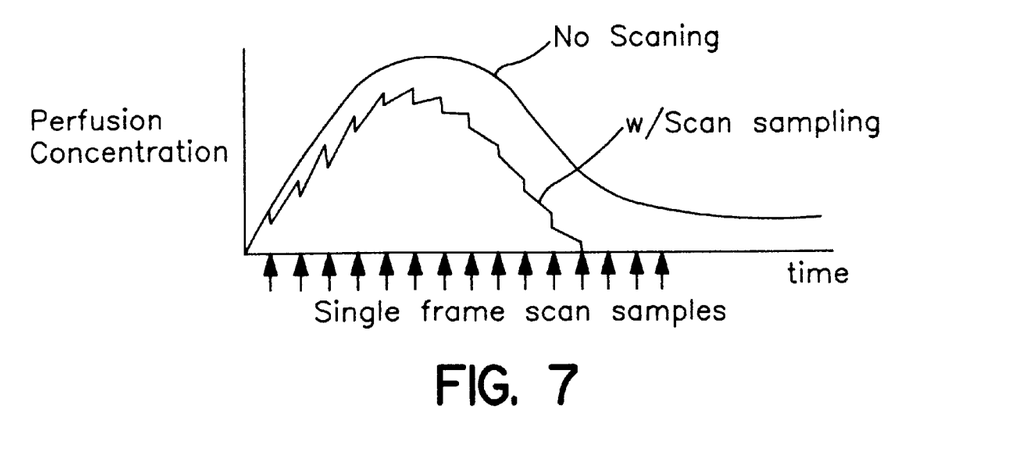
FIG. 7 illustrates the timing of an exemplary scanning sequence and the desired effect on the concentration of contrast agent in comparison to the concentration of contrast agent without scanning.
Figure 8:
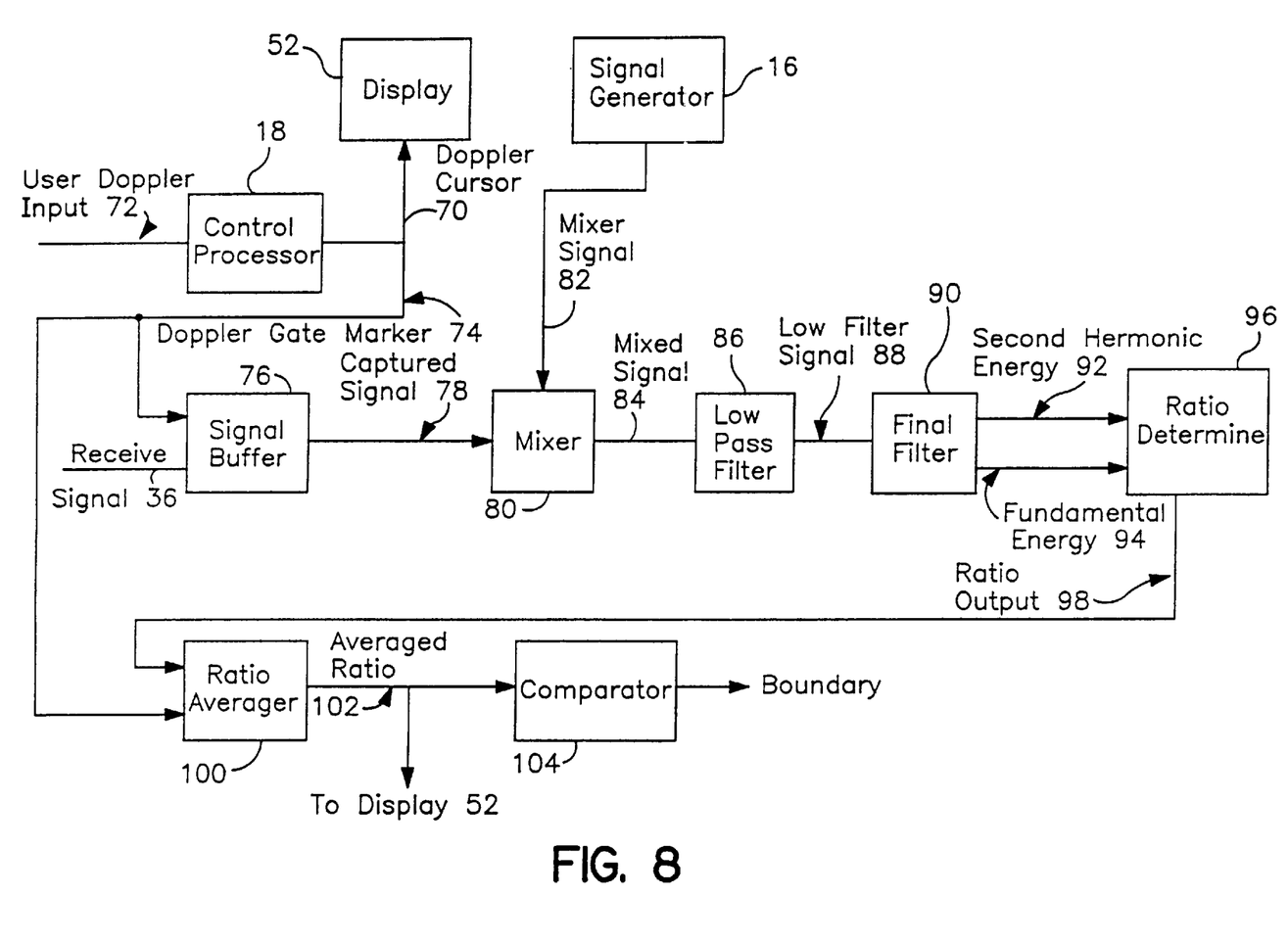
FIG. 8 is a diagram of a system for spectral content measurement.

2. A Method for Controlling Contrast Agent Concentration for Intensity Linearity (FIGS. 6, 7 and 8)

As has been described, it is known that the concentration of contrast agent in a region of interest is critical to the images obtained therefrom because the intensity of the image, that is, the amplitude of the Receive Signal 32, will increase with an increase in concentration of the contrast agent up to a certain point, and will then plateau. As a consequence, too low a concentration will result in poorly enhanced images. Too high a concentration, however, will result in "washing out" of at least portions of the image as the concentration of agent in the corresponding volumes of tissue reach the plateau concentration so that various volumes of the tissue cannot be distinguished by differences in concentrations of the agent.

As has also been discussed, while there are various reasons for this effect, one is that the saturation of agent particles in a given region results in interference between the particles that reduces the total reflection. This effect appears to become significant when the concentration is such that the particles or bubbles are, on the average, within one transmit frequency wavelength of each other. Another reason is a shadowing effect wherein the ultrasonic energy is absorbed or reflected by the agent in a bolus or body of the agent in the near field of the line, that is, when a volume of agent that is nearer to the transducer than the region of interest generates a return that overshadows the return from the region of interest. Since the ultrasonic energy that reaches the region of interest is thereby attenuated more than what would normally be returned from the effects of the tissue in the region of interest, the return signal is of a lower intensity than normal and the density of contrast agent in the region of interest is therefore underestimated. Accordingly, and for example, a spatial average measure of intensity in a region of interest that included a shadowed region would underestimate the concentration of contrast agent therein, resulting in degradation of the resulting image.

Figure 6:
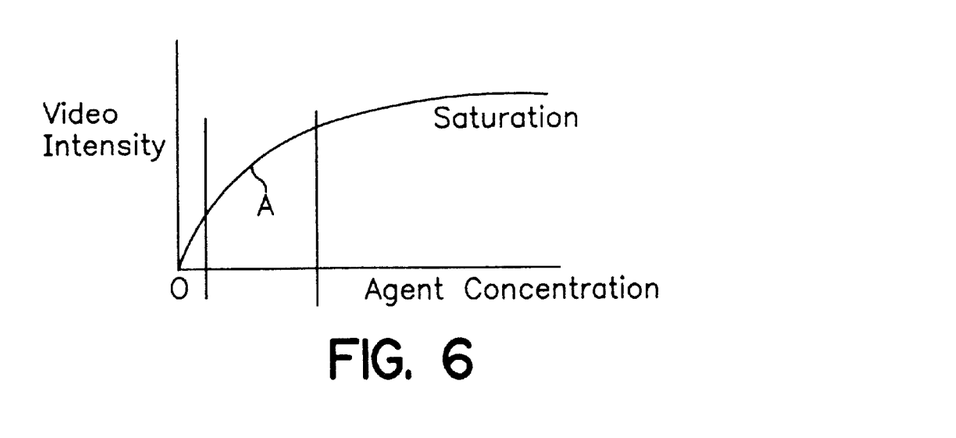
FIG. 6 illustrates the linear response range of a contrast agent.

Both of these effects can be minimized if the concentration of contrast agent in the region of interest is controlled to fall within a generally linear range of contrast agent response, illustrated in FIG. 6. In general, it is known that the concentration of contrast agent in a given region can be reduced by insonication of the agent at a sufficient power level, and generally will be reduced under normal scanning, and, of course, that the concentration can be increased by injection of more agent into the region. In this regard, for example, it is known that the modes of operation commonly referred to as "scan freeze mode" and "EKG triggered mode" can be used to prevent the destruction of contrast agent in the region of interest, and thereby increase the return signal from the contrast agent during subsequent scans.

The method of the present invention, however, provides a more precise measurement of the concentration of contrast agent in the region of interest or between the transducer and the region of interest for the purpose of selectively destroying contrast agent to a point that facilitates imaging and measurement and suppresses the shadowing effect while not severely dimming the perfusion bloom in the region of interest.

The concentration of contrast agent, and the rate of destruction of contrast agent in a region, can be determined as a function of the power level of insonication, or the proximity of the transmit frequency to the resonant frequency of the bubbles or particles of contrast agent, or the rate of scanning, that is, the number of scan frames executed per second, or by a combination of any of these factors. For example, the transmit power could be controlled and varied from frame to frame, or the transmit aperture could be varied from frame to frame, as will be described in a following description of an improved method for using contrast agents. Further, the transmit coefficients can be updated during scanning to control the transmit frequency on either a portion of the scan lines or a portion of the frames, or both, resulting in a mixed transmission spectrum. Finally, the scan rate, that is, the frame rate, can be controlled either during the frames by inserting "blanks" or by delays between frames. FIG. 7, for example, illustrates the timing of an exemplary scanning sequence and the desired effect on the concentration of contrast agent in comparison to the concentration of contrast agent without scanning, that is, as the agent washes into and out of the region of interest.

It will be appreciated that any of these factors may be controlled manually by a user, for example, by corresponding control inputs to Control Processor 18 or by direct control inputs into, for example, Signal Generator 16 or Drivers 28. These factors may also be controlled by a predetermined profile, that is, a Control Processor 18 program stored in Program Memory 20 and defining a predetermined sequence of power levels, frequencies of transmission or scan rates.

Preferably, however, each of these factors, or a selected combination of these factors, would be controlled by a system-generated profile that is generated dependent upon the characteristics of Receive Signals 34, that is, by "feedback" from the received signals. For example, and referring to System 10 as illustrated in FIG. 1, Signal Processor 40 may directly or indirectly determine the current concentration of contrast agent by direct operation upon Receive Signal 32, such as measurement of the dynamic level of Receive Signal 32, frequency dependent determination of signal levels at the transmit frequency and the agent second harmonic resonant frequency, and measurement of in-phase and quadrature components of the received signal.

In other implementations, the relative concentration of contrast agent may be determined by Data Processor 50 measurement or comparison of Images 48 from Frames 46 or of Images 48 from successive Frames 46, for example, by determining the dynamic range of intensity of Images 48, that is, of the maximum and minimum intensity levels within the images relative to the average intensity level of the images. The resulting measure of contrast agent concentration, represented in FIG. 1 as Concentration Feedback 68, may then be provided to Control Processor 18 to, in turn, execute a program controlling the transmit power, the transmit frequency, or the scan rate, or a combination thereof by controlling, for example, Signal Generator 16 or Drivers 28.

In accordance with the present invention, for example, wherein the level of transmitted power is controlled over time to achieve the above described results, the level of transmitted power may be controlled by either of two methods, or by the combination of the two methods. In the first, the received signal level is divided by a power reduction ratio, such as the time interval elapsed since the last scan, thereby re-normalizing the signal level at each scan and compensating for the effects caused by variation of the transmitted power. In the second, the transmitted power is increased from scan to scan, but only sufficiently to maintain the agent level at a concentration short of saturation.

Finally, it is preferable that the function controlling the destruction of contrast agent to reduce the shadowing effect be synchronized with EKG Signal 56 to maintain consistency in the measured concentration profile across a series of cardiac cycles.

3. Contrast Agent Detection Using Spectral Content Measurement (FIG. 8)

As described above, it is advantageous to have a machine executed process for measurement of the concentration of contrast agent in a region of interest, for example, to determine the amount and rate of perfusion in the region of interest, as described above, or to control the rate of destruction of contrast agent in a region of interest, as also described above.

In this regard, it is well known and understood that normal tissues without contrast agent produce some second harmonic response to the excitation frequency of the ultrasonic lines, but that the proportion of second harmonic energy increases dramatically with certain contrast agents. Therefore, and according to the present invention, it is possible to detect the proportion of increase of signal and image intensity in a region of interest due to the presence of a contrast agent, and only due to the contrast agent, by analyzing the spectral content of Receive Signal 38 for the fundamental and second harmonic components.

According to the present invention, therefore, the ratio of energy in a frequency band around the second harmonic of the resonant frequency of the contrast agent to the energy in a band around the fundamental resonant frequency of the contrast is calculated, thereby allowing the contribution of the contrast agent to be discerned from that of the tissue. Then the concentration of contrast agent may be assumed to increase proportionally as the ratio of second harmonic component to the fundamental component increases during perfusion.

It is preferable, as illustrated in the representation of System 10 shown in FIG. 8, that the spectral analysis be performed on the direct, beam-formed, that is, time aligned and summed, received signal, before spectral information is lost due to receive filtering, analytic detection, compression and other processing by Signal Processor 40. As shown therein, the scan signal data is gathered from a single line, or lines, selected by use of a Doppler Cursor 70 that is controlled by a User Doppler Input 72 and displayed in Display 54 by Control Processor 18. Control Processor 18 generates a Doppler Gate Marker 74A, corresponding to User Doppler Input 72 and Doppler Cursor 70, and provides Doppler Gate Marker 74A as an input to a Signal Buffer 76 connected to receive Receive Signal 38 to capture Receive Signal 38 in a region around Doppler Gate Marker 74A, represented as Captured Signal 78, whereupon the scanning may be conditionally restarted or delayed for later re-start. Captured Signal 78 within the region, which for example, may be approximately 2 cm wide along the scan line, or line, is then mixed in Mixer 80 with a sine wave signal from Signal Generator 16, identified as Mixer Signal 82, at the second harmonic frequency to generate a Mixed Signal 84. Mixed Signal 84 is then low pass filtered by Low Pass Filter 86 which, for example, may be a 32 point digital FIR and the resulting band-limited signal, indicated as Low Filter Signal 88 is squared and spatially averaged in Final Filter 90 using, for example, a box-car filter, and the resulting output, indicated as Second Harmonic Energy 92, is a measure of the second harmonic energy within the frequency band around the second harmonic versus axial position along the scan line as Doppler Gate Marker 74A is moved along the scan line.

The process is also performed with Mixer Signal 82 at the fundamental resonant frequency of the contrast agent, either at the same time as Second Harmonic Energy 92 is determined or as a separate process, and the resulting output of Final Filter 90 will be Fundamental Energy 94, which will be a measure of the fundamental frequency energy within the frequency band around the fundamental resonant frequency of the contrast agent versus axial position along the scan line as Doppler Gate Marker is moved along the scan line.

Second Harmonic Energy 92 and Fundamental Energy 94 are then provided as inputs to Ratio Determiner 96, thereby providing a Ratio Output 98 which represents the proportion of second harmonic energy versus position.

Ratio Averager 100 is then connected from Ratio Output 98 and from Doppler Gate Marker 74A to select, for example, a 1 cm portion of Ratio Output 98 and calculates and stores an Averaged Ratio 102 for each Ratio Output 98. The capture and signal analysis procedure then repeats at an interval selected under program control and for a number of iterations selected under program control. At the conclusion of the iterations, the Averaged Ratios 102 are displayed through Display 54 as the average harmonic ratio versus time along the scan line, thereby displaying the contrast agent concentration as a function of time.

Finally, it should be noted that although the function elements necessary to practice the method just described have been described as additional logic elements added to System 10, these functions may also be performed largely through the existing components of System 10, in particular using the general purpose programmable functions of Control Processor 18, as may the functions described in the following descriptions. Also, the doppler gate method of locating the region of interest could be replaced with any of several alternate user interfaces.

4. Tissue Boundary Detection Using Spectral Analysis With A Contrast Agent (FIG. 8)

As has been discussed previously, a contrast agent injected into a vein eventually fills, for example, the left ventricle of the heart, the coronary arteries, and the myocardium, and the rise in Receive Signal 32 level components at the second harmonic from the presence of the contrast agent in these regions results in a near uniform level of brightness in the Images 48 presented on Display 54 after signal processing, such as detection, logarithmic processing and compression. In particular, the border or boundary between the cavity of the left ventricle and the tissue of the myocardium is lost, since both are at an equal or nearly equal level of fundamental and second harmonic brightness due to perfusion of the contrast agent into the tissues.

It is advantageous, however, to be able to determine boundaries of the myocardium and to thereby isolate the myocardium as the myocardium is a region of primary interest for determining perfusion by the method described herein above. It is further advantageous to be able to determine the boundaries of the myocardium in real time, because the shape of the heart changes continuously during a cardiac cycle and as the patient ventilates.

In this regard, it has been found that the proportion of fundamental frequency energy in the left ventricle is significantly less than the proportion of fundamental frequency energy in the myocardium tissues, both before and after the introduction of a contrast agent. According to the present invention, this difference can be used to determine the border between the left ventricle and the myocardium by, in effect, filtering the effect of the contrast agent out of Receive Signal 32.

This process may be accomplished using the spectral analysis method and apparatus illustrated in FIG. 8, but, in this embodiment, having the user first select a line or line that is known, for example, from Images 48 as displayed on Display 54, to pass through both the myocardium and the left ventricle and therefore through the boundary between the left ventricle and the myocardium. As described herein just above, Averaged Ratios 102 will then represent the average harmonic ratio versus time for a small region defined by Doppler Gate Marker 74A and along the scan line passing through the myocardium and the left ventricle and the boundary therebetween.

When used to detect the boundary between the myocardium and the left ventricle, the region for which Averaged Ratios 102 is determined is moved along the scan line or lines by incrementing or decrementing the position of a Doppler Gate Marker Sub-Window 74B and the value of Averaged Ratio 102 is determined by Comparator 104 at each position along and compared to preceding values as Doppler Gate Marker Sub-Window 74B moves along the scan line. In this regard, Doppler Gate Marker Sub-Window 74B is a sub-window of data along the scan line and with the outer data window located by Doppler Gate Marker 74A.

Comparator 104 then determines the position along the scan line or line of the steepest increase or decrease in the value of Averaged Ratio 102, depending on where in the image the border appears or which border is to be observed, and this position thereby represents the boundary between myocardium and the left ventricle since any variations in the value of Averaged Ratio 102 within each region by itself will be significantly less steep than the change in Averaged Ratio 102 at the boundary. The spectral analysis circuitry illustrated in FIG. 8 may then be used further to confirm the boundary by performing the same analysis along neighboring scan lines, and may be used in the manner described just herein above, and by suitable positioning of Doppler Gate Marker 74A and thus of the Averaged Ratio 102 window, to measure the rate of perfusion in a selected area of the myocardium tissue as described in section B. 1. of the present description.

Finally, it should again be noted that although the function elements necessary to practice the method just described have been described as additional logic elements added to System 10, these functions may also be performed largely through the existing components of System 10, in particular using the general purpose programmable functions of Control Processor 18, as may the functions described in the following descriptions. Again, the doppler gate method of locating the region of interest could be replaced with any of several alternate user interfaces.

Figure 9:
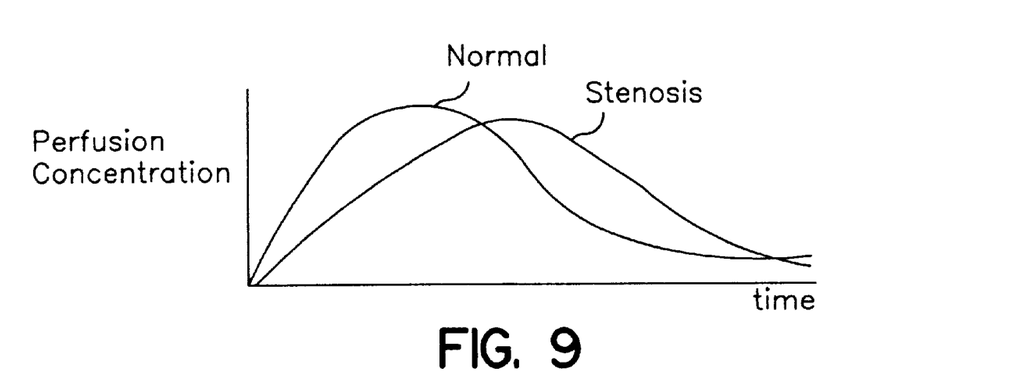
FIG. 9 illustrates a bolus of contrast agent over time.

5. Scan Triggering to Generate A Bolus of Contrast Agent (FIG. 9)

It is known that a contrast agent may be introduced into the heart by means of aortic route injection, that is, injection into the aortic artery, and that the concentration of contrast agent versus time in the left ventricle will then approximate a step function. This concentration versus time profile is desirable for measuring perfusion in the myocardium because, as illustrated in FIG. 9, the steep ramp of the contrast agent concentration versus time profile is visible in well perfused regions of the myocardium whereas the concentration versus time profile will be flattened in poorly perfused regions, as in the case of a flow-limiting stenosis of the coronary artery.

Injection by the aortic route, however, is invasive and only venous injection is practical in diagnostic settings. Venous injection is disadvantageous, however, because the contrast agent is required to pass through the blood vessels of the lungs, which smooth the shape of the contrast agent bolus, and the left ventricle is flooded with contrast agent at the same time the myocardium is perfused, so that the resulting bloom of the Receive Signal 32 return obscures the boundary between the left ventricle and the myocardium. In addition, there is only one observable perfusion per injection of contrast agent because the contrast agent must "wash out" and be consumed or destroyed before the next perfusion ramp and be injected and observed.

Therefore, while certain aspects of the present invention that have been discussed previously hereto provide methods for eliminating or at least reducing certain of these problems, it would be advantageous to be able to create a well defined bolus of contrast agent in the regions of interest.

According to the present invention, a well defined bolus of contrast agent may be generated in the region of interest with venous injection by scanning the region of interest continuously and at relatively high power levels to destroy the contrast agent entering the region of interest at a rate to keep the concentration of contrast agent in the region at a low, steady state level. The steady state level is monitored, for example, using the method described in section B.3 herein above, until a predetermined time has passed since the contrast agent was injected, the end of that time being designated by the user of the system as the beginning of perfusion of the measurement period, whereupon System 10 begins scanning in the pseudo-triggered mode described in section B.2 herein above and the steady state level becomes the initial contrast agent concentration level in the perfusion profile measurement as described herein above.

This method may therefore be viewed as the reverse of the "freeze mode" method of scanning to image the contrast agent. In that method, the System 10 is kept in the "freeze" mode until the concentration level of the agent has reached a relatively high level. System 10 is then taken out of "freeze" mode and into scanning mode to image the accumulation of contrast agent in the region of interest. Instead of keeping the System 10 in the "freeze" mode while the concentration of agent builds up, however, the present method continuously destroys the agent in the region of interest until a specified time has passed or a low level of concentration has been detected, yet agent entering the region of interest is still at a high level of concentration, and then imaging at a rate as described in Section B.2 to observe and measure the perfusion process. It will be noted that the depletion of agent according to this method creates a new bolus each time it is executed, thereby allowing multiple imaging from a single injection of agent.

As has been described herein, and for example, a bolus of contrast agent that is venously injected reaches the region of interest as a "spread out cloud" with diffuse edges so that the concentration of agent entering the region of interest increases gradually rather than as a step function. The depletion method described just above, however, may also be used to "cut off" the edges of the cloud until the portion of the spread out bolus of agent entering the region has reached the concentration desired, at which point the destruction of agent ceases, or at least is significantly reduced as the System 10 is switched to normal scanning mode. The sharp edge of the bolus formed by the destruction of the sloping leading edge of the bolus thereafter enters the region of interest as a step function.

Lastly in this regard, it should be noted that a new method of selective drug delivery is being studied wherein agents consisting of micro-bubbles similar to those of contrast agents are modified to contain not just air or inert gas but pharmaceuticals. The selective target agents are tagged in various ways, well known in the relevant arts, to collect in specific tissues or disease sites in the body. The shells of the bubbles may then be opened, or burst, by insonication by any of the methods described herein, thereby releasing the pharmaceutical only locally and in the specifically targeted tissues or disease site.

6. Rapid Depletion of Contrast Agent by Non-Imaging Scans

Finally, and as discussed elsewhere herein, a sufficiently high concentration of contrast agent in the near field of a transducer tends to absorb the acoustic energy of the scan beam in the near field of the acoustic transducer, thereby not only shadowing the agent in the far-field of the transducer beam but also resulting in a disproportionate depletion of the agent in the near field relative to the depletion of the agent in the far field. This differential depletion, in turn, interferes with the detection and measurement of the agent in the far field.

According to the present invention, however, unwanted agent depletion patterns may be compensated for by the use of non-imaging, depletion scans of relatively high power levels selected to rapidly deplete the agent. According to the present invention, the acoustic beams may be de-focused to effectively "erase" the agent in the field of the defocused depletion scan, or selectively focused into selected regions or areas of the imaging scan field to selectively deplete the contrast agent in the selected regions or areas. The selective focusing of depletion scans can thereby be used, for example, to deplete the contrast agent concentrations in the imaging scan far field to levels corresponding to those in the imaging scan near field or to otherwise create desired patterns of contrast agent levels or patterns of contrast agent depletions in selected regions or areas of the depletion scan field.

Because the depletion scans are not used for imaging, and do not result in an image display being generated from the depletion scans, the return signals need not be received or processed, there need be no delay between non-imaging scans for reverberation decay, and the depletion scans can be generated using a different transmitted spectrum than would be optimal for imaging scans but which is optimized for agent depletion. As such, non-displayed depletion scans can be executed quickly, for example, between or interleaved with normal contrast imaging scans or the sets of scan lines that form an image frame, and in any desired or selected pattern or sequence, and depletion scans may, for example, be executed during an entire separate frame from the imaging scans. With the sole restriction that a depletion scan will not be executed at the same time as an imaging scan or so as to interfere with an imaging scan, depletion scans may be executed independently of and separately from imaging scans and may differ from imaging scans in one or more characteristics, such as arrangement or sequence, frequency or frequencies, pulse lengths, number of pulses, power levels, focus profiles, apodization or aperture.

The ability to rapidly execute depletion scans is of advantage in, for example, the image subtraction process discussed elsewhere herein as minimizing the time between the scan data sets is significant for the suppression of temporal artifacts due to heart motion. The depletion scans can thereby be inserted between the imaging scans, so that the delay between imaging scans is no more than a few tens of milliseconds. It should be also be noted, however, that, because of the need to complete the execution of the depletion scans between imaging scans, it may be necessary to limit the depletion scans to particular sector regions of interest, rather than the entire imaging scan field. In such instances, the sector regions in which the depletion scans are executed may be selected, for example, by an on-screen display of a doppler cursor line or a scan wedge.

Finally, it should be noted that because the depletion scans need not be sharply focused, the transducer drive waveform voltages may be increased above the levels used in image scanning, thereby permitting a stronger transmitted signal and greater depletion of the agent.

Lastly, while the invention has been particularly shown and described with reference to preferred embodiments of the apparatus and methods thereof, it will be also understood by those of ordinary skill in the art that various changes, variations and modifications in form, details and implementation may be made therein without departing from the spirit and scope of the invention as defined by the appended claims. For example, it will be noted that in several of the above described presently preferred embodiments of the present invention it is described that the energy levels of the fundamental and second harmonic frequency components of a returned signal are determined by first and second harmonic component energy detectors that mix the returned signal with fundamental and a second harmonic mixer signals. It will be recognized by those of ordinary skill in the relevant arts, however, that there are several other alternate and well known methods for detecting fundamental and second harmonic frequency component energy levels that may be used for this purpose. In further example, it has been described above that depletion scans are not used for imaging and do not result in an image display being generated from the depletion scans. It will be recognized, however, that in certain instances or applications it may be necessary or desired to use depletion scans for imaging and thereby to processes the depletion scans in generating an image display. In such cases, it may therefore be necessary to process the depletion scans in a manner to compensate for or to accommodate the differences from the normal image scans regarding the depletion scan signal power levels, pattern or sequence of depletion scan transmissions, and the frequency or frequencies, pulse lengths, number of pulses or focus profiles of the depletion scans. Therefore, it is the object of the appended claims to cover all such variation and modifications of the invention as come within the true spirit and scope of the invention.

What is claimed is:

1. In an acoustic echographic imaging system including a transducer for transmitting an acoustic imaging signal and receiving a return signal representing an image along a scan line, the return signal including contributions from a contrast agent, and a processor for generating the acoustic imaging signal and extracting from the return signal information representing the concentration of contrast agent along the scan line wherein the contrast agent is depleted by an amount related to the power level of the acoustic imaging signal insonicating the contrast agent, a method for controlling the concentration of contrast agent within a range of generally linear response, comprising the steps of:

determining from the return signal the relative concentration of contrast agent along the scan line, and from the relative concentration of the contrast agent, adjusting the characteristics of the acoustic imaging signal to increase depletion of the contrast agent when the concentration of contrast agent is higher than the linear range of response and decreasing the depletion of the contrast agent when the concentration of contrast agent is lower than the linear range of response.

2. The method of claim 1 for controlling the concentration of contrast agent within a range of generally linear response, wherein the step of adjusting the characteristics of the acoustic imaging signal further comprises:

adjusting the received signal by dividing the received signal by a power reduction ratio that is a function of the time interval elapsed since a previous acoustic imaging signal transmission to re-normalize the power level of the received signal.

3. The method of claim 1 for controlling the concentration of contrast agent within a range of generally linear response, wherein the step of adjusting the characteristics of the acoustic imaging signal further comprises:

increasing the power level of a next acoustic imaging signal by an amount to deplete the contrast agent from a saturation level of concentration.

4. In an acoustic echographic imaging system including a transducer for transmitting an acoustic imaging signal having a fundamental frequency and receiving a return signal representing an image along a scan line, the return signal including contributions from a contrast agent, a spectral content measurement processor for detecting the concentration of the contrast agent along the scan line, comprising:

a gate marker generator for generating a gate marker window for selecting at least one scan line and a position in the gate marker window along the selected scan line, a signal buffer connected to receive a return signal along the scan line and responsive to the gate marker signal to capture the return signal in the gate marker window, a second harmonic component energy detector for providing a second harmonic energy signal representing the second harmonic energy within the frequency band around the second harmonic of the captured return signal versus axial position along the selected scan line as the gate marker window is moved along the selected scan line, a fundamental frequency component energy detector for providing a fundamental frequency energy signal representing the fundamental frequency energy within the frequency band around the fundamental frequency of the captured return signal versus axial position in the gate marker window and along the selected scan line as the gate marker window is moved along the selected scan line, a ratio determiner for receiving the fundamental frequency energy signal output and the second harmonic energy signal output and generating a ratio output that represents the proportion of second harmonic energy to fundamental frequency energy versus position of the gate marker window along the selected scan line, and a ratio averager for receiving the ratio output and responsive to the gate marker window for selecting in a sub-window of the gate marker window the ratio output along the scan line and generating an averaged ratio output for each selected window of the ratio output wherein an averaged ratio output represents the concentration of contrast agent in the selected window.

5. The spectral content measurement processor for detecting the concentration of the contrast agent along the scan of claim 4, wherein:

the spectral content measurement processor repeats the generation of the averaged ratio output at each iteration of the acoustic imaging signal so that the averaged ratio output for each selected window represents the averaged harmonic ratio versus time along the scan line, thereby representing the contrast agent concentration along the selected scan line as a function of time.

6. The spectral content measurement processor for detecting the concentration of the contrast agent along the scan of claim 4, wherein:

the second harmonic component energy detector includes
 a second harmonic mixer for mixing the captured return signal and a second harmonic mixer signal to generate a resultant second harmonic mixed signal,
 a low pass filter for filtering the resultant second harmonic mixed signal to generate a band limited low filtered second harmonic signal, and
 a final second harmonic filter for squaring and spatially averaging the low filtered second harmonic signal and providing the second harmonic energy signal output, and the fundamental frequency component energy detector includes
 a fundamental frequency mixer for mixing the captured return signal and a fundamental frequency mixer signal to generate a resultant fundamental frequency mixed signal,
 a low pass filter for filtering the resultant fundamental frequency mixed signal to generate a band limited low filtered fundamental frequency signal,
 a final fundamental frequency filter for squaring and spatially averaging the low filtered fundamental frequency signal and providing the fundamental frequency energy signal output.

7. The spectral content measurement processor for detecting the concentration of the contrast agent along the scan of claim 4, further including a boundary detector for detecting a boundary between regions of interest, comprising:

the gate marker generator for selecting a scan line passing through the boundary between the regions of interest and for incrementally stepping the gate marker sub-window along the scan line, and a comparator for comparing the values of the averaged ratio at each step of the sub-window along the scan line and identifying the point of greatest change in value of the averaged ratios along the scan line, thereby identifying the point of greatest change in value of the averaged ratios along the scan line as the point of the boundary between the regions of interest.

8. In an acoustic echographic imaging system including a transducer for transmitting an acoustic imaging signal having a fundamental frequency and receiving a return signal representing an image along a scan line, the return signal including contributions from a contrast agent, a boundary detector for detecting the boundary between regions of interest, comprising:

a gate marker generator for selecting a scan line passing through the boundary between the regions of interest and for incrementally stepping a gate marker window along the scan line, a signal buffer connected to receive a return signal along the scan line and responsive to the gate marker signal to capture the return signal in the gate marker window, a second harmonic component energy detector for providing a second harmonic energy signal representing the second harmonic energy within the frequency band around the second harmonic of the captured return signal versus axial position along the selected scan line as the gate marker window is moved along the selected scan line, a fundamental frequency component energy detector for providing a fundamental frequency energy signal representing the fundamental frequency energy within the frequency band around the fundamental frequency of the captured return signal versus axial position in the gate marker window and along the selected scan line as the gate marker window is moved along the selected scan line, a ratio determiner for receiving the fundamental frequency energy signal output and the second harmonic energy signal output and generating a ratio output that represents the proportion of second harmonic energy to fundamental frequency energy versus position of the gate marker window along the selected scan line, and a ratio averager for receiving the ratio output and responsive to the gate marker window for selecting in a sub-window of the gate marker window the ratio output along the scan line and generating an averaged ratio output for each selected sub-window of the ratio output wherein an averaged ratio output represents the concentration of contrast agent in the selected sub-window, and a comparator for comparing the values of the averaged ratio at each step of the sub-window along the scan line and identifying the point of greatest change in value of the averaged ratios along the scan line, thereby identifying the point of greatest change in value of the averaged ratios along the scan line as the point of the boundary between the regions of interest.

9. In an acoustic echographic imaging system including a transducer for transmitting an acoustic imaging signal having a fundamental frequency and receiving a return signal representing an image along a scan line, the return signal including contributions from a contrast agent, a spectral content measurement method for detecting the concentration of the contrast agent along the scan, comprising the steps of:

generating a gate marker for selecting at least one scan line and a position along the selected scan line, capturing the return signal as a captured return signal in a region around the gate marker, generating a second harmonic energy signal representing the second harmonic energy within the frequency band around the second harmonic of the captured return signal versus axial position along the selected scan line as the gate marker is moved along the selected scan line, generating a fundamental frequency energy signal representing the fundamental frequency energy within the frequency band around the fundamental frequency of the captured return signal versus axial position along the selected scan line as the gate marker is moved along the selected scan line, generating a ratio output representing the proportion of second harmonic energy to fundamental frequency energy versus position along the selected scan line, and selecting a window of the ratio output along the scan line and generating an averaged ratio output for each selected window of the ratio output wherein an averaged ratio output represents the concentration of contrast agent in the selected window.

10. The spectral content measurement method for detecting the concentration of the contrast agent along the scan of claim 9, further comprising the steps of:

repeating the generation of the averaged ratio output at each iteration of the acoustic imaging signal so that the averaged ratio output for each selected window represents the average harmonic ratio versus time along the scan line, thereby representing the contrast agent concentration along the selected scan line as a function of time.

11. The spectral content measurement method for detecting the concentration of the contrast agent along the scan of claim 9, wherein:

the step for detecting second harmonic component energy further includes mixing the captured return signal and a second harmonic mixer signal to generate a resultant second harmonic mixed signal, low pass filtering the resultant second harmonic mixed signal to generate a band limited low filtered second harmonic signal, squaring and spatially averaging the low filtered second harmonic signal and providing the second harmonic energy signal output, and the step for detecting the fundamental frequency component energy further includes mixing the captured return signal and a fundamental frequency mixer signal to generate a resultant fundamental frequency mixed signal, low pass filtering the resultant fundamental frequency mixed signal to generate a band limited low filtered fundamental frequency signal, and squaring and spatially averaging the low filtered fundamental frequency signal and providing the fundamental frequency energy signal output.

12. The spectral content measurement processor for detecting the concentration of the contrast agent along the scan of claim 9, further including the method for detecting the boundary between regions of interest, comprising the steps of:

selecting a scan line passing through the boundary between the regions of interest and incrementally stepping the gate marker sub-window along the scan line, and comparing the values of the averaged ratio at each step of the sub-window along the scan line and identifying the point of greatest change in value of the averaged ratios along the scan line, thereby identifying the point of greatest change in value of the averaged ratios along the scan line as the point of the boundary between the regions of interest.

13. In an acoustic echographic imaging system including a transducer for transmitting an acoustic imaging signal having a fundamental frequency and receiving a return signal representing an image along a scan line, the return signal including contributions from a contrast agent, a method for detecting a boundary between regions of interest, comprising the steps of:

selecting a scan line passing through the boundary between the regions of interest and incrementally stepping a gate marker window along the scan line, capturing the return signal in the gate marker window, generating a second harmonic energy signal representing the second harmonic energy within the frequency band around the second harmonic of the captured return signal versus axial position along the selected scan line as the gate marker window is moved along the selected scan line, generating a fundamental frequency energy signal representing the fundamental frequency energy within the frequency band around the fundamental frequency of the captured return signal versus axial position in the gate marker window and along the selected scan line as the gate marker window is moved along the selected scan line, generating a ratio output representing the proportion of second harmonic energy to fundamental frequency energy versus position of the gate marker window along the selected scan line, selecting in a sub-window of the gate marker window the ratio output along the scan line and generating an averaged ratio output for each selected sub-window of the ratio output wherein an averaged ratio output represents the concentration of contrast agent in the selected sub-window, and comparing the values of the averaged ratio at each step of the sub-window along the scan line and identifying the point of greatest change in value of the averaged ratios along the scan line, thereby identifying the point of greatest change in value of the averaged ratios along the scan line as the point of the boundary between the regions of interest.

14. In an acoustic echographic imaging system including a transducer for transmitting an acoustic signal and receiving a return signal representing an image along a scan line, the return signal including contributions from a contrast agent when a contrast agent is present along the scan line, a signal generator for generating the acoustic imaging signal at controllable power levels, a method for creating a well defined bolus of contrast agent in a region of interest being scanned with the acoustic imaging signal, comprising the steps of:

introducing a flow of contrast agent into the region of interest,     scanning the region of interest with an acoustic signal having a power level selected to destroy the contrast agent entering the region of interest at a rate to keep the concentration of contrast agent in the region of interest to a predetermined low, steady state level, and     after a predetermined time has passed since the flow of contrast agent has begun, the end of that time being designated by a user of the system as the beginning of perfusion of the region of interest by a flow of contrast agent of a desired concentration, beginning image scanning of the region of interest at an acoustic imaging signal power level less than that selected to destroy the contrast agent.

15. The method of claim 14 for creating a well defined bolus of contrast agent in a region of interest being scanned with the acoustic imaging signal, wherein the steps of scanning the region of interest with an acoustic signal to destroy the contrast agent and scanning the region of interest with an acoustic imaging signal further includes the step of:

detecting the concentration of the contrast agent in the region of interest by measuring from a return signal from the acoustic signal the spectral content of the return signal to determine the concentration of contrast agent in the region of interest.

16. In an acoustic echographic imaging system including a transducer for transmitting an acoustic signal and receiving a return signal representing an image along a scan line, the return signal including contributions from a contrast agent when a contrast agent is present along the scan line, a signal generator for selectively generating the acoustic signal at selectable power levels, durations and intervals, a method for generating desired contrast agent depletion patterns in a region of interest, comprising the steps of:

scanning the region of interest with an acoustic imaging signal and processing the return signal thereof to produce an image of the region of interest, and     scanning at least a selected portion of the region of interest with an acoustic depletion signal having a power level and duration selected to create a desired contrast agent depletion pattern wherein the acoustic depletion signal is not used to produce an image.

17. The method for generating desired contrast agent depletion patterns of claim 16, further comprising the step of:

generating and transmitting the acoustic depletion signal in the interval between the acoustic image signals.

18. The method for generating desired contrast agent depletion patterns of claim 16 wherein:

acoustic depletion signals differ from acoustic image signals in one or more of the following signal characteristics: arrangement, sequence, frequency, pulse lengths, number of pulses, power levels, focus profiles, apodization and apertures of the depletion acoustic signals and acoustic image signals.

19. In an acoustic echographic imaging system including a transducer for transmitting a plurality of acoustic scan lines to form an acoustic scan and receiving a return signal representing an image along a scan line, the return signal including contributions from a contrast agent when a contrast agent is present along the scan line, a signal generator for selectively generating the acoustic scan lines at selectable power levels, durations and intervals, a method for compensating for unwanted contrast agent depletion patterns in a region of interest and resulting from destruction of the contrast agent by the acoustic signal, comprising the steps of:

producing acoustic imaging scan lines and processing return signals thereof to produce an image of the region of interest; and     producing acoustic depletion scan lines in at least a selected portion of the region of interest, the acoustic depletion scan lines having a power level and duration selected to create a desired contrast agent depletion pattern, wherein the acoustic depletion scan lines are not used to produce an image.

20. The method for compensating for unwanted contrast agent depletion patterns of claim 19, further comprising the step of:

generating and transmitting the acoustic depletion scan lines in the interval between scans of the region of interest with the acoustic image scan lines.

21. The method for compensating for unwanted contrast agent depletion patterns of claim 19 wherein:

the acoustic depletion scan lines differ from the acoustic image scan lines in one or more of the following signal characteristics: arrangement, sequence, frequency, pulse lengths, number of pulses, power levels, focus profiles, apodization and apertures of the depletion acoustic signals and acoustic image signals.

* * * * *